US006312951B1

(12) United States Patent
Morris et al.

(10) Patent No.: US 6,312,951 B1
(45) Date of Patent: *Nov. 6, 2001

(54) EXPRESSION AUGMENTING SEQUENCE ELEMENTS (EASE) FOR EUKARYOTIC EXPRESSION SYSTEMS

(75) Inventors: Arvia E. Morris; Chi-Chang Lee, both of Seattle; James N. Thomas, Redmond, all of WA (US)

(73) Assignee: Immunex Corporation, Seattle, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/435,377

(22) Filed: Nov. 5, 1999

Related U.S. Application Data (63) Continuation of application No. 08/785,150, filed on Jan. 15, 1999, now Pat. No. 6,027,915, which is a continuation-in-part of application No. 08/586,509, filed on Jan. 11, 1996, now abandoned.

(51) Int. Cl.[7] .................................................... C12N 5/10
(52) U.S. Cl. ........................ 435/358; 435/320.1; 536/24.1
(58) Field of Search .............................. 536/24.1; 435/6, 435/320.1, 252.33, 358, 69.1

(56) References Cited

U.S. PATENT DOCUMENTS 5,081,018    1/1992   Grummt et al. .

FOREIGN PATENT DOCUMENTS 0306848    3/1989   (EP) .

OTHER PUBLICATIONS

Beitel, L., et al., "Sequence requirements for the stimulation of gene amplification by a mammalian genomic element," *Gene 102*: 149–156, 1991.
Gasser, S. and Laemmli, U., "A glimpse at chromosomal order," *Trends Genet 3* : 16–22, 1987.
Grosveld, F., et al., "Position–independent, high–level expression of the human β–globin gene in transgenic mice," *Cell 51*: 975–985, 1987.
Hemann, C., et al., "High–copy expression vector based on amplification–promoting sequences," *DNA Cell Biol 13*(4): 437–445, 1994.
Holst, A., et al., "Murine genomic DNA sequences replicating autonomously in mouse L cells," *Cell 52*: 355–365, 1988.
Kaufman, R., et al., "Improved vectors for stable expression of foreign genes in mammalian cells by use of the untranslated leader sequence from EMC virus," *Nucleic Acids Res 19*(16):4485–4490, 1991.

Kellum, R. and Schedl, P., "A position–effect assay for boundaries of higher order chromosomal domains," *Cell 64*: 941–950, 1991.
Klehr, D., et al., "Scaffold–attached regions from the human interferon β domain can be used to enhance the stable expression of genes under the control of various promoters," *Biochemsitry 30*: 1264–1270, 1991.
McArthur, J. and Stanners, C., "A genetic element that increases the frequency of gene amplification," *J Biol Chem 266*(9): 6000–6005, 1991.
McArthur, J., et al., "Elements which stimulate gene amplification in mammalian cells: role of recombinogenic sequence/structures and transcriptional activation," *Nucleic Acids Res 19*(9): 2477–2484, 1991.
McBratney, S., et al., "Internal initiation of translation," *Curr Opin Cell Biol 5*: 961–965, 1993.
Meyer, J., et al., "Inhibition of HIV–1 replication by a high–copy–number vector expressing antisense RNA for reverse transcriptase," *Gene 129*: 263–268, 1993.
Phi–Van, L., et al., "The chicken lysozyme 5' matrix attachment region increases transcription from a heterologous promoter in heterologous cells and dampens position effects on the expression of transfected genes," *Mol Cell Biol 10*(5): 2302–2307, 1990.
Stolzenburg, F., et al., "Structural homologies and functional similarities between mammalian origins of replication and amplification promoting sequences," *Chromosoma 103*: 209–214, 1994.
Wegner, M., et al., "An amplification–promoting sequence from mouse genomic DNA: interaction with a trans–acting factor that also affects gene expression," *DNA Cell Biol 9*(5): 311–321, 1990.
Wegner, M., et al., "Interaction of a protein with a palindromic sequence from murine rDNA increases the occurrence of amplification–dependent transformation in mouse cells," *J. Biol Chem 265*(23): 13925–13932, 1990.
Wegner, M., et al., "Cis–acting sequences from mouse rDNA promote plasmid DNA amplification and persistence in mouse cells: implication of HMG–1 in their function," *Nucleic Acids Res 17*(23): 9909–9932, 1989.
Weidle, U., et al., "A new expression system for mammalian cells based on putative replicator sequence of the mouse and a truncated thymidine kinase gene," *Gene 73*: 427–437, 1988.
Weidle, U., et al., "Amplified expression constructs for human tissue–type plasminogen activator in Chinese hamster ovary cells: instability in the absence of selective pressure," *Gene 66*: 193–203, 1988.

*Primary Examiner*—James Ketter
(74) *Attorney, Agent, or Firm*—Janis C. Henry; Simone L. Jones (57) ABSTRACT

There are disclosed nucleotide sequences which can improve expression of recombinant proteins two to eight fold in stable cell pools when present in an expression vector.

11 Claims, 1 Drawing Sheet

FIGURE 1A

FIGURE 1B

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 14507 base pairs
      (B) TYPE: nucleic acid
      (C) STRANDEDNESS: single
      (D) TOPOLOGY: Not Relevant    (ii) MOLECULE TYPE: DNA (genomic)

(iii) HYPOTHETICAL: NO

(iv) ANTI-SENSE: NO

(vi) ORIGINAL SOURCE:
      (A) ORGANISM: Chinese hamster    (vii) IMMEDIATE SOURCE:
      (B) CLONE: 2A5-3 lambda CHO sequence    (xi) SEQUENCE DESCRIPTION: SEQ ID NO:1:

```
GCGGCCGCGA GCTCTAATAC GACTCACTAT AGGGCGTCGA CTCGATCTCC AGGGTCTAAG    60

GACCCCACTT GACGCAATGA ATTTTGTTTC AGGATAAGCT AGAAGCCAGA AGCTGCTAAA   120

GAAAGTTACC ATCTGTTAAA AACTGCAGCC AAGATTTGTT GTTTGTTTGT TTCCGAGAAA   180

GGGTTTCTCT GTGTAGCCCT TGCTGTCCAG GAACTCAGAG ATCCACCTGC CTCTGCTTCC   240

TGAGTGCTGG GATTAAAGGT GTGTGCTGAC TACAGGCAAG CTTGTTTGTT TATTTGTTTG   300

TTTGTTTGTT TTTCAAGACA GGGTTTCTCT GTATAGCTCT GGCTGTCCTG GAACTTGCTC   360

TGTAGACCAG GCTGTCCATG AAGTCACAGA GATCTGCCTG CCTCTGTCTC CCTCCTGAGT   420

GCTGGGATCA AAGGTGTACA CCATCACCCA GTCCCCACTC CCCCCCCCAC CTCCCAGCAC   480

AGGCAAGGTT TTTAATGTAT AGACTCTGCA TAATATTCCA GTTCCTTTGG CCATATATAC   540

AAGGATGGAA AAAATACCTG AAAATAATGG TTTTTATTTT GGTCATGGAA TTTTAATACA   600

TTTTTCTTTA TTCATTTCAG TGTCTTTCAA ATCCTAACAT TTTGGCTACA GAATTAAAAA   660

AAATAATAAC TGACCTTAAA CTTCCATGTC TGTGATAAGG GTACATTTGT TATTATTGGA   720

GGATAAACTG TTACTTCACC AAATGTTACT TGTAAATGTG CTGTTCACCA TGCATCTGGC   780

TGCAGTTTCT CTAGGCCCTT TGGCCTATTG ATTGTTGTCT GCTTCTTAAG TTAGCTCCTA   840

GGACCTCTGG ACAGCCTCAT CTGGAGCTGC GGCTGCTGTT GCCCTTCCTC TGTAGCTGTC   900

CATGTTGCCT CTGCAGTATT TGCTTTCCTT GTCCTTGTTT GTGCTGTTCA TTGCTAGTTG   960

TACTCCAATA TGCAAATTTT TGAAAACTTT TTCAGTAACA TTATCCTAAT TGTTCCTTTT  1020

CGTTTATAAG TAGTTTACTT TCTTTACATA ATTTTCTTAG GACTGATGCA TTTCAATTGG  1080

CTTTTTTTTG TGACAGGGTC TCTTGTTGCT CAGGCTAGCC TTGAGCTCCC AGTTCTCCTC  1140

AAATCCTCAA ACTTTATGGT AAAGAAGACC TAAGTTTATC ATGGGCAGCC ATATATGCTG  1200

ATTATCCTTT CCTTATAATA TATAATATTG TTATTCATGT AGAAGGAGCT CTTTAATGCC  1260

ATTTTGTTAA ACAGCCAACT ATTTAGCATA TTAGCTGTTC ATATTTTATA GTTTTTAAGA  1320

GCTCTTTTTG GGGATCATTA TGAATTTATA GAGAAAAGTT TGGTTTAACT AGTTAGCCAT  1380

AGAAATGGAT AGACTATTCA GTTGGATAGG AAGCAGTATG TTACTTATGC TGTCATAATT  1440

GCAGTGTACA AGAACCCAGC AAAATGGTAG TGGTGTTGGG GAGGAAAAGT GACAACATTG  1500
```

-continued

```
ACTCTTTGGT GGACAGCAGA GCATAGCTAT ATTATTTGGT TTTTCGAGAT AGGGTTTCTC   1560

TTGTAGCTTT GGAGCCTATC CTGGTACTCC CTCTGGAGAC CAGGCTGGCC TCGAACTCAC   1620

AGAGATCCGC CTGCCTCTGC CTCCCAAGTG CTGGGATTAA AGGCGTGTGC CACCAACGCC   1680

TGACATTAAG TTTTCTGACA CTGTCAGGAA TTGTCACTTC TGCTTCTCAG TTTCCTTCTC   1740

TGAAAAATGA GGAGAAAGGT ATCTAGGCTG CCTCCTCATT TCTGACTAGT TTTGTTTGTT   1800

TGTTTTGAGA CAGGGTCTCT CTCATTTGGT AGTCTTGGCT GGTGTGGAAC CAGGCTTATC   1860

TTGAACTCAC AGAGATCCAT CTGCTTCTAC GCCTTGAATG CCGGGATTAA AGGATGTGCA   1920

TAATTTATAG ACTAGTTTTA GGAAGGGAAA AAAAAAAGAC TATGGTAGAA GAAATTGTGG   1980

AAGTGTTTTA TTATACCTGA AAGTCCTTTG TGGCAATTTT GGCATGGTTA GGCAAAGTTT   2040

AAACATCCCA GTCATCAAAT AGATTACATC ACGACATTCC TATGGCTTAT CCCGGACTCA   2100

TAAAAGTATT TTATGATTCA CTTAAAGATT TAATAGTGAT TTGGATTACT TGTGTGGGAA   2160

AACACAAAAT GAGGCTGTAG TATCTTACAG TGTCAGAAAC AATACTTTAA AAACCTACTG   2220

GGATCCTGTT AGAGGACCCT TAAAGAGGCC CCACTGGGCA GAGCTAGAAT CAGATGAGCC   2280

ACGAGAGAAG GAATGTGGAC TATTGCTTTT AAGTATGAAG TGAGCCCACA TCTCTGCTAT   2340

AAATGATATA AATGAATGGG GGGGTAGTCT ACCTTATGGA AGAACTCCAA AACTTTATGT   2400

AGCTCTTGCA ACTTCATGGA GAAAGTGAAG TATGGTATCC TGAACTGGGA TCTAGAATAC   2460

AAAGATGACA TGTGCAGAAA GCATTCTAAA GTCCAAGTGA AGTTTGGAGT TTAACCAATG   2520

TTAATTTTTA ATTTTGACAA GTGTACCATG GAAATAAAAA ATATTAACAG TTGGGGGGAG   2580

GGAGCTAGGA GAATGAGAAG GGGAAAAGAG GAGGGGTGTG GAGGACATGA GGGAGCAGAA   2640

AGGTTGAGTC AGGGGAAGAA TAGAAGATAA CAAGAATGGA GATACCATAA TAGAGGGAGA   2700

CATTTTAGGA TTACAGAGAA ATCAAGAAAC TAGGGAAATG TCTGGAGATC TACAAAGATG   2760

ACACTAGCTA ACAATCTAAG CAACAGAGGA GAGGCTACCT TAAATGCCCT CCCCTGATAA   2820

TGAGATTGAT GACTGACTTA TATGCCACCC GGCACCCACA ACTAATCACT GAACTGAACT   2880

GGAATCCAGT TGCAGAGAAA GACAAGTGAT GACCAGGCTG GTGAAACCCA CAGAAACAGC   2940

TGACCTGAAC ATTGGGGAGC TCTTGGTCCC CAGACTGAAT GCTGAGATAA CAGCATGGGA   3000

CTGATCCAGA CCCCAGAAAC ATGGGTTTCA GTGAGGAAAC CTTGGAAATC TACGGGACCT   3060

CCTGTAGTAG TTCAGTACTT ATCCCTAGCA TAGGTGTGGA GTTTGGGAGC CCATTCCACA   3120

TAGAGGAATA TTACCTGAGC CAAGACACAT GGGGGTGGGC CTAGGCCCTA TCCCAATAGA   3180

CTCTGATGAC ACCCTATTTA AAGCCTCACC ATCCAGGGGG AGCAGGAAGG ATATGTGATA   3240

GGTAGGGTTT TAGTTGGGGG TGGTGGTGGT AAGGGAGGAT GGGTGGGTGT GGGAACTGGG   3300

ATTGTCATGT AAAACAATCT TGTTTCTAAT TCAAATAAAA TCTACAGAAA AAATAGTAAC   3360

AGTTGGGAAA ATGAGTAAGA AGTAGTCAGG ATCTTTCTAT TCTGAGATTA AAGTTTACCC   3420

TTTTAGAAAA GGCTGGGGAT ATAACTTAGT GGTAGAGTGC TTGCCTTGCA TGTCCAGGTC   3480

CCTAAATTCA AGCCCCAGTA CTACAGAGAT ACATACATAC ATAGAAGATT TAACAGACTG   3540

TGCTTGCAGA CCCAGTTTCA TTTTAGCCAG AGATATAGTG AAACTCTATC TCAGTATGTT   3600

CCTATCACCC GCATGGTTAG AAATAGTTGA TTTTAAATAT AAAATCTAAG TGAACTTGTA   3660

GAGAATATGA GGAATTAAAA GTAGAAGGTT GATTTTGGTT CAAAGGGATT TCCAGTTCCC   3720

CAAGTGGTAC AAGATGTTTG CAAGGGGCA CAGTAAAGAA ACTGTGCTGA CATAAACACA   3780

CTATGATATG ATAACTGTTT TTATTGTAGG GAAGAGAGAG AGAGGAGAGA GAGAGAGAAA   3840
```

```
GAGAAAGAGT GATTTAACAA GTACTTGTGA TACTGAAGGA GCCTGGAGGC TGTCATGGGT      3900

TTTGATATGC AATCACAGGT ATATATCAGT GGAGAGCCAT ATGTACCTTC TGCCAGAGGT      3960

AAGGGTAAGG AAAATGAGTC ATTTTGGCAG ACTGAAACTG GTTTCCCAAG TTCCTGAGAA      4020

ATTCTGGTGT TTAACTACCA GAAATTCTAT AGTCTGGCTT GAGTTCATTT CTGGGTATAC      4080

AGACTGCCTT TTGGAGTTTG GGATTTGGAG TTTATTTCCT TTGGACTGAC AGTTGAAAAT      4140

ACAAATCACC TCACTTGGTT ATCATCTTTG GATTTTGACT GCTTTTTAGA TGAAACTTGT      4200

TCCCATGACC ATGCAGACAT CATTATGGTG TGTATGTGTA TATGTAATTA TGATGCTGTA      4260

TATACTCAGT TTTGTAGATT TAATTTTAAC TATGTATTTT CCAAGATTTA ATTTTAACTA      4320

TGTATTTTCC AGTCCACAAG TAATTATTAG ACTACTTTAT GGACCAGATA CCAAGATAAG      4380

TACACTTGGG ATAATGGATG AGTGAGAATG CTGTGGGTCT TTGTTTGGAG GTTGTTGATA      4440

TCTAGGGAGA GATGATGTAC TATCTAGGGA TGATGATTGT GAGAGCATGT AAATCGTAGA      4500

ACCAATGACA TGTCTGTCCT TCAAGGCAAG TGAAAGAAGG AAGCAGTAGA CTGGTGCAAT      4560

GGGAGCTGGA ATACAGTGTT CACTTGGAGG CAGAGCATCA GCTAGTGCTG AAGCCTCATA      4620

GTGTGAAGCG CCAGGGAGGA ACAGTGTCTG GAGTGCAGAG AATGGGCCTT TAGAAAGGAA      4680

TAGCCAGAGA CTGAAGAAAT AGCAAAGTAA GAGCTTAATC ATGAAACTTA GCCTGGGCGT      4740

TCCCTTGAAA GTGATGGAAC TCACTGAGAA TACTAAAGCT AGGCAGTGAT AAAAGGAGCC      4800

TGCTGTGGTG TGGCAAATA GATGGGCAAG TGGTGAGAAG TCCTGGACCT GGTAGTGTGT      4860

TAAAAGTGAT AGTAAAATAC AAGCTGTTTG TAATTGCTGC CTGCTGGGAA AGGAAAAAGT      4920

CACTTTTTTC CCCAATGGAG TGTCAATGGG TATATCAACT ACACTCCACA AAATGAACTC      4980

CATGAAATTT TTATGGGCTT TTTGTTTTAT TTGTTTTGTT AGAGAGAGAG AGAGATAGAG      5040

ATAGAGAGAG AGAGAGAGAG AGAGAGAGAG AGAGAGAGAG AGAGAGAGAG AGAGAGAGAG      5100

GAGAAAGAGG CCTTTAGAGA GACAATTAAT TTTGGGTTTG TGGTGAGGTA GGGAAGATCT      5160

GGGAAGAGTT GGGGAGGAGA AAATATGACC AAAATATATT GTATGAAAAC AAGATATTGT      5220

AAAACAGGAG ATTATTGCTA GAATATAACA GTTGAAATGC TAGGAGTTGG AGTTGGTTGC      5280

TTTTATAACT GATAATGAAG TTGGGTGTTC CTACCTCAGG TAAAAAAAAC TCCAGCACAG      5340

TAATCCAAGA GTAGCCATTT GTACAGTGTC CTTGTTTGTA GTTTTAAGAG CAAAAGAAAT      5400

TGTTTTGTAG TAGAAAGTTG TGGTGTTGCT CAGAAACCAA ATAAAGGAAT TCTGAGTTAG      5460

AATCTTTTTA TTTGGCAACA GCATGCTGAC TGTGAGAGAT GACAAGCTGC TTTTGACTGT      5520

ATTGTTTTAC TTGGTATCCA CCAATAGCAT TGGTGGTACT ATTCTACTGA GATGTGCCAG      5580

CACCATGTCA CATTGGGTAC CATAAACTCA CTAGCCATAC ATTGAGAATC TTTGGGAAAG      5640

GCTGGTTTAG AAGCTGTGAT GACTATTCTT GGTTGTCAAC TTAACTATAT CTGCAATGAA      5700

CTGTAACCCA GAGATGGAGG GCACACACAT GATCCGGATC TTGAGACTGG TTGACACGTC      5760

CTTTAATCCA GCCCTTGCTT GAGGCTGGAG GGTACACCTT TAATCTGGCT ACACCTTCTG      5820

CTGGAAGGAC AATTGAGGAA AGAAGGGGTG TGTTTGTTCT TGGCCTGTTT TCCCTCGTCT      5880

TGTCAGCACA TCCATTTCTT TCACTGGTAT TGGAGTCTAC TTCTTTGGGA TTTTATCATA      5940

TACAGAAGAC CAGTTGAGAT GCTGAGTCTC CTGGGACTGG ATCCTTGGAC TTTTTATTCA      6000

CAGGTAGGCA TTGTTGGACT GCAGCCCTTA AGTCATTCCA ATATGGGAAT ATATATATTC      6060

TAAAAGTTAT ATATGAATGA ATATATATAT TCATTCTATA AGTTCTGTGA CTCTAAGAGA      6120

CCTGACTAAT ACAGAAACTT TTTAAACACT TTTTAGTTTT CATTGTATGT ATGTTTTGTA      6180

TGTGCTTGTG AGTGCAGATG CTCATGGCTG CAGAGGTATG GAGTCCCTAC AGTATTTAAC      6240
```

-continued

```
ATTGTTAAAT TTCTTTTCCT GCTTTCACCA CTACTTCTGT CGTTAACTGG CTTGTTGTGA    6300

TAGGTGGCTG TCCTAGTTAG GGTGGCTATT GCTGTGGTGA AACACCATGA CTAAAGCAAC    6360

TTGGAGGAAA GGGTTTGTTT GACTCACAAT TTTATGTAAC AGTCCATCAT TATAAGCAAT    6420

GAGAGTAGGA CCTCACACAG GGCAGGACCT GGCAGAACCC ATGGAGGAAT GCTGCTTACT    6480

GGCTTGTTCC CCATGGCCTG CTCAGCATGA TTACTTATAG AACCCAGGAC CACCAGCTCC    6540

AGTATGGCCC CACCCACAAT GGGTTGAGTC CCCCCACGGT AACCACTAAT TAAGAAAATG    6600

CCCTACAAGC TTGCCTATAG CCCAACCTTA TGAAGGTATT TTTTCATGTG ACAAGGTGAC    6660

ATAAAATTAG TCAGCACAGT GGCCAAGCCT GTATCTTTGA GACTCCCAGG CCCCAGCTTT    6720

GCCTAACTGT ATTTAATGTC TGCCTGTTGG AGAGAAGTCC AGATGCTTTC AAATGGTCTA    6780

CTCAGACTTA TTTTTAGAAA TAAACTATTC CAAAGTTCAT CTGGTACTTA TTCTAAGCAA    6840

GGTCATGCTC TTCATGCATT TGATAGCCTT CACCCTGTTG TCAGTTCCCT TGTAAACATT    6900

TTCTGCACCC ATATCCCCAG GCTGTTTATT TAGAGCAACC TACTTAATGC TAGTAGAATT    6960

AGAGGACCGC CCAAATGGGT GCATTCATGT AACAGGAAGG TGGTACATTC AGAGAAAATT    7020

AAAATACGTT AAATTTATGC AGTGCTGTGA TTTGGAATGT TTTAAATGTA CTAGGAAAAA    7080

GAACTTGGAG ATCTGTTGGT TCCTGCCTGG ATAAAATGAG CCTAAGTACC AATGAAATCC    7140

TGAAAATACC GAATTGGTAT TACTGGAAAG AAGTGTTTGT TTTTTATTAC ACTACTGGAC    7200

TTGGCTATTT GTATCTAAAA TCCCATCTGC AAATGTTGCC TTAGCACAGT AAAACAGTAA    7260

GGTATTGAAA AGGTTCAAAA AAGTGCAAGT CATTGAATAC TGTGTTATAT TTGCTCTACC    7320

CCTTGGTTAG GTGTGAAGGA GTGAGCATAA CAAATCCTAA GTGAGTGAGT CAGTTGTCTG    7380

TTTTTCTGTT GTGTATTTGT TTTGTGATTC TTGATTTCTT TAAAAGATTT TATTTATTTA    7440

TTGTATACAA CATTCTGCTT CCATGTATAT CTGCACACCA GAAGAGGGCA CCAGATCTCA    7500

TAATGGATGG TTGTGAGCCC CCATGTGGTT GCTGGGAATT GAACTTGGGA CCTTTGGAAG    7560

AACAGTCAGT GCTCTTAACT TCTGAGCCAT TTCTCCAGCC CCGTGATTCT TGATTTTATC    7620

TTCTACTTTC TGCAGAAAAT ATTTTAAAAC TGGAATTAGA TGGTTTGGCT CTTTGGCTTT    7680

CCATTCCAAT TGAGTACATT TAAGGCTGTA AATTTCCCTT TAGGTAATAT TGAATCTTTA    7740

TGCTGTTATC TTTAGTTATC ATCATCATTG TTATTTTACC TTTTACAATA GTATTTACTT    7800

TAGTGGACAT GACCAGGCTG AGCTGGGCTA TGTGGGACAG GGAGGGGAGG GGAGAGAGGA    7860

ACCAACTGCA GCACCCAGGA GGCCAAAGGG ACAAGAGGGA AAGGGGTGGG TAACCAAAAT    7920

GTCTGGTTTG TATAGGAAAA AGCTCTGGAG GAAGGGTGGG GAATGACAGC CATACCTTGG    7980

AACAGTTAGG GACTGAGGAT GCTGGAAGAA CCTGTTGGCC ATATCTAGCT TTAATATGTT    8040

AAATAGGCAC CTCAGCTGTT TGTCCTGGAT TTGAAATTTA ACAAAAAGAT AGTAGTTTTC    8100

TTAGGTCATT AGTGTTATAT GTGACCAGGA GGCTGGAGCA CCACAATATC ACAATACAAA    8160

TAATCTGGTT TAGCCAGGCT TCCATATGAG GTTGATGTTT GACTAGAAAA GGGTTTGCAA    8220

GCCCTGTGTG TTACCTCCTG GCTTGTGATT TTGGTTCTTC AGAGTTTCCC CCTTAAGCCT    8280

TAACTGCTTG TTGTGTTCAA GAATTCAGGA CTTTTAGCCA GGCTTGGTGG CAGGAGGCAG    8340

AGGCAGTCGG ATCTCTGTGA GTTCGAGGCC AACCTGGTCT ACAGAGCAAG TTCCAAGACA    8400

GCCTCGCAAG CTACACAGAG AAACCCTGCC TGGAAAAACA ACAACAACAA CAACAAAAAC    8460

AAAATAAAAG AATGGGCAGG CTTTGAGGTT TCCAGTGCTG ACATACTGTC CAGTGTCTCA    8520

GTTGATGTCT TGTTGCCTAC AAAATGTAAG AACTCTCAGC TCCTCCAGCA CCACGCTGCC    8580
```

-continued

```
ATGTCTCGCC ATGATGACAA TGAACTGGAC CTCTGAAACT ATAATTGAGC CACCCCAATT   8640
AAATGTTTTC CTTATATATA TAAAAAAAAA GAATTCTGAA CTTTTCTTTT GTTCCCTTCC   8700
CTTCTACCAC ACCCTAATTG TAATCCATTT TAATTTCCTG GTCACAGTCC TGTCTCTCCT   8760
TCCATTGTAC CTTGCCCTTT TCTAAAGAGC GACTGCAAAG TATGTTTGCG TAGGTGAGGA   8820
TCTAAAACTT TATGAGGTAC GAACATCACA GAATTACTTT GTAATTTCAG TTTATTGTAG   8880
GCTTGGCTTT TTGGGGAGGG TTTACGTCTT AGACCTCTTA GTGCTTCTTT GTTTCATGGT   8940
GTTCTAACTT CGAAGCATCT CTGTAGCTTT AATGGATTCC TTTTCTGAAA GCTTTGCTCT   9000
CTTTCTTCCC CCTCGGCTTT TCTTAGGCA AGAGGGCTAA CTGTAAAGTA AGGCTTACTG   9060
CCTTGTGTTT CCAAATGTGT CCGAAGAGGA AGTGTCTTCT GTGAATCCTG TTATGCATGA   9120
ATAACAGGAA ATAGAAAGAA ATTCACTTTC ATTATTATAA AAGTAATATG TTCGTTTAAA   9180
AAATTCTAAT GAAGAGCTGG AGATGCAACC CAGGGGTAGA GCACACACTC AGCATGCAGG   9240
AGGCCCTGGG TCCAATCTTG GAATCTCCTC TCAGTTAACC TGATCTCTAG CTGATTAGTA   9300
GTGAGTGCAA GCCCACTTTC CTCTTCTGCC TCATTGCTCA GTGATAACAG CTGTTAAACT   9360
TTGTCTTATT CTAAAACTAC CTCTGTGCAA ATGCTAGCAC AATAATATAT ATCATATGCA   9420
CATGATTTTT TTTTTATCTT GAAAAGTAAG TCAGTATAGC TACAAAGTTC ACTTGGCATT   9480
GTCAACATTT CACAGGCGTA ATATTCCTCC TCTAGTACTG TCCTCTTCAT TCTTTGTGAC   9540
CAAGTTTGGA GAGAGTGCAC AAATGCCAGG GAGGTTTGTG GGAAGGTTTC TCATGTTCTG   9600
GTAAGGCGAG TAAGAAAATA GTCTCATGCA GGTGAAATGA GTGCTATGCA GTATATATTA   9660
TACCAGAGAA CAGCAAATGA CCAAATTCAC ACTGAACTAG TTCAGTAAAA TTGGCTTTGT   9720
CAAAGCTTTC CTTGCTTAAA ATGTAATTCC CTGTCATCCT AGTTCTGGTC TGGATTCTTT   9780
TCCTGGAGTC TTGACTTCCA GATTCCCTGT GGACTTTTGT TTGAGTTTCA AGCTTTTGAA   9840
ATATAGAAAC CTATCTAACT TAACAAACTT GGGAGAGAAA AGACTCCAGA ACAACTGAAA   9900
ACAGACCAGG CTAAATGAAT AGACTTTATT CCTCTCTTCT TACCTGCAGT TTTCAGATAT   9960
GCAGAGTTGG AGCGGATCTT AGAGGTTGAT TCATTCATGC CTGAAGAAAA CACATTTTAT  10020
AGACCCTGTG CCCAAGTTCG TGGTGGACAT CACCCTTTAT TTACTAATTG CACTACATAA  10080
CAGGCATTTT AGAAGACTGC TCCAGTCAGA GACCCCGCCT TAGAGGAATC TGTAAACCCT  10140
GAACTCCTAT CACTCATGAG CACTAGTTAT GTTTGGAATG CCGTATTAAA ACAAAAGTTA  10200
CATTTCTAAA CTTAAAATTT TCTAGCACAG AGACAGTGGG AGTAGCTAAC TTTGATAGAC  10260
ATTTTTCTAC TAAAAGTCTT TCTAAGTACA TAATCTTCTG TAAGTTGGAA AACAGCAAAA  10320
TAGAACGTCT CCTACGTAGT TAATCTTTTT GCATAAATTTG CACATGTAGG AGTTATTAGT  10380
ATACGGGTAA GTTTTCACTT TTTCCCCCAA CTGGAGTGTC TTGTGGCTGG GTTTGAAAAA  10440
GGGAACGGGA GGCCGCTGGA GGGGATTGGT AAATGAGATA AAACACCACT CATTCAACTC  10500
AGTGACTCAG CATTTAAATT TTCCATAAAA GGATTAAAGG AAAATTAAAC AAATTCTTAA  10560
AGCCAAGACT CTGGAGAAAC TTGTTGGTGT GCTTTAGTTT TCACTGTTAT GACTCATGAA  10620
TTTATGCATA AATTAGTACA TTTATAAAAA CATAGCCTTT TTAGAGTTTT CTGTTTGGCT  10680
AAAGTGCCAT TGTTAGCATT TGGAATTACC TTTTTATGTC TTATATTTTT TCCAAATAAA  10740
AATAAATGTT TCTGCTGTCT TACTACTGAA ACTACGTTGT GAGCACTTTA AATTTCTCAA  10800
AGCAGTTTCG CCTGTTATAC TTGGCGCTTA GTCATCGTCG TACACAACAG GACCTGATTA  10860
AGAAGGCTGT GCTGCCTCTA AGCCGGGCTA GATTGTAGCC ACTAGCAACC AGGCTGCAAT  10920
AATTTCCCTT TGATGACATC ATCCACTGTG GAAGAACCCA GTTGCTTCAG CCAGTCGAAC  10980
```

-continued

```
TATACAGTTC CAACCTCATC AAATATGGCA TCTCCCTTGC CTGCTATAGC AGGGGGAGGA    11040

AAAAATGCCA CCATCTTTTT AATCTAGCAA GCTTCTCTTT TCTTCATCTT TTTTTTTTTC    11100

TTTTAAAAAA ATTCTGATCA TGGATGCTTC TTCCGATCCC TATTTGCCTT ATGACGGGGG    11160

AGGAGACAAT ATCCCCTTGA GGGAATTACA TAAAAGAGGT AAGAGCATCC CCTTGCTCTG    11220

AATCCTCTGT TGGTTGTTGT GCATGCGGCT GGGCGGTTCT GGGGACAGGC TGTCTGTTGT    11280

CCTCTTGCTG CAATGTGCTG CTTAGTTGCC CTGCCTTGTT GCTGTGGGAG AATGCGACCT    11340

TCCCAGCAGG GCTGGCCCTC CCTGATTGTT TGCTCTGTGC AGATTAGCCC TGCTTCAGAT    11400

CACATAGGGC TGCAGACTCC ATCTTCTGTG TGAAAATGCT TTCGGTTTGA TTGCAGAAAT    11460

AAGCTGCCTT TACAGCCAGC TAAAGTCCTG GTGGTTGGTT GGCACCTGCA AGTAGTATT     11520

TTTGTACCTC TGGAAACTTA TATTTTCTTT ACACAGCAAT ATCAAGTGCC GGTATGCCAT    11580

TCTGTTTTGG CTGCTGCCAA TTACCATGTA GACTTTGCAC CACAGAGTAA TAGTAAAAGC    11640

TCCTAGCTGC ATTTTATAAC ATTTAAAAAT AGCAGGAAAG AAGAATTATT TTTGATTTAA    11700

CATGTTTTTG TCATTTAACG TCTTAACTGA TTGACATACT ATATTGTCTG TCTCGTGGGT    11760

ATCTTGTACA ACTTGATAGG ATAAAGCAAT TTAGTTTTTT TTTTTTTTTT TAAATACATC    11820

CAGAATGTAA GTCGTCAGTA GTTTTCGAAC AGATAAGTAA TGGTGTTAAT CTTTTGGCAG    11880

GCTTTGCCTT GGTCTCCTTA AAGCTAATTA GGTGTTACTT AATTAAACTG CTCTTTTGCT    11940

CATTTTCTTA AATTATTTTT TTAAAAGATA GTTGGCATTT GCTGTTCTAG AAATAAACTT    12000

CAAGAAACAT TCTTTAGCCA GATGACTTCA TGTATGAGCC ATGTTAGTTT GAATTATTTG    12060

CTTGGTGTTA TAAACTTTAT GGTTAATAC CAACTTTTAT TATGTTTACA AGGTAAATAA     12120

GGAAAATTTC AAGTACATTT TGTATCCTGA GAACAAATTT AAGTTCCATA GAATTTAGGA    12180

ATTACAATGT ATTCAACAGA TACTTACTTG TCATACTGTG CCTGCAAAAC AATAATTAGA    12240

CTCTGAACAG GTGCAACAAT TTTCTGTAGA ATTCTGTGCT TAGTAAAAGG TTGCTTTTTA    12300

TATTTTGAGA GAAATCTATT TAAAGATCAT GGCCCATATT TTGTGCATAT TTTTTTCTGT    12360

ATACCATTTC CATATATGTG TGTGTGTGTA CATATATGTA TATATATAAA ATGTTAGAAC    12420

ATTTGAGGAA ATAGCTAAAA GTACAAAAGT AATGTTTTCT AATTTTTTAC TCCCCGAGGT    12480

TATTTCTTTT TTCCTTGTTT TCCTTTCTCT TTGTTCCTAT CATCAGTTTC TAGTAATACT    12540

CTTATTGAAC AGTGATTATT CAAATGTCAC ATTATTTATT AATCAGCATT TAAATGGTAA    12600

AACCAGACAG ACCATACTTT CTCTGAGTGA TGACAACATC CATTTTTAGT AATGATAAAC    12660

TAGAAGGGTC AGGCTTGATA GTCTTTGTCA GGACTAATTT ATAGACTGTA AAGGCCAAAA    12720

GAAATAAGAA ATGTCAAAAC TCTTGTGAAA CTAGACATAC AGATATTACC AAGAGAGAAA    12780

CTAGAAAAAA AAATTCTGTG ACATGGCCTT AATTTGCCAG GCACCATCGT GAAGGCCTAA    12840

ACCCTCTTA GAAGCTCACT CAGATGCCAT CCTGCTTCTC TGATGAGACT TCCTGTCAAT     12900

ACAAACATGG TTTAGGAAGA ATGAGTGTTT GCAGTATAAA CCAGTTATTT ACTAGCCTTA    12960

CTTTAAGAAT ATACTGTAGT GTCCTTGAGA GAGAAGGTGT TTGTTTTCTG TAATTTATGA    13020

CCCTTTTGAA ACCATAGATC AGCACAAAGG AACTGGGGAT ATGGAAATGG GAACATAACT    13080

TAAATCCAGA AAAGTGAATC AGATTCCCTG TGAGGACAAA ATGCAATATT TAGAAATAGG    13140

ATCTTTAGGC TGGGAGGGAG AAAAGAGGAA AAAAATGAAA GTATAACATT TTTCATAAGT    13200

ATAAGATTTC ATAAAAAAAT GAAATCTATA ACATAGAGGG TGTTGATAAA GTAAGCATGG    13260

ATATGTTTAG TAAAGCCGAC AGAGCTAAGA ATTAGCTTTG TGAGTAATTG GACTTAATCA    13320
```

```
AACTTTTCAA GGTGGGATAC AAATGAATAA TTGTAGAATA AATGGATAAA AGAATATGAA    13380

TAAAATGAAT AGTGAGTAAA AATTAAAAAT GAAGCTTTTT ACTTAAGTGC ATATTGTAGT    13440

GGCTAGAACA AATAGATTCA AAATAGAAAT CATTTATATA TTCTTGATTA GAAGATAAAA    13500

TGTTATTTTA GAAATAGCCA TCTTTGGAAG TAAATTTGCT ATGTTGAACA ACCAGGTTTT    13560

CATAATTTGT CTCTTATTTT TTTTCAGGAA GAAAAAAAAA CTTGACTTAT TTGTACTGCT    13620

AAGTTTTATT CAATGTGCTT GCTTGCTTAA ATTTTTAATG AAGTTTTAGT CATTTGGTGG    13680

TCAAATTCCT TTTATCTACT AATCGCTTTT CGTGGCTTTG GCTTTTAAAA TTGTATTTAC    13740

TGCATTTATT TGTGTGTATT AGGAGTCAGG TGGCCATATG TGCCATGGCA TGTGTATGGA    13800

AGCACTTGTG GACATGAATC TTCTCTTTCC ACATGTGTGG GCCACTGGAA TCAAACTAGT    13860

GTCAGGCTTG GCAGCAATTT TTAATGCACT GAGCCTTCTC ACCACCCCCT GGACTTTTGT    13920

GGGGCAGAAG GGGACAAGTT TAATATTTTA TTTACTCCAT GTAGAAAGCC TTTAAAAAAT    13980

GTAGAAAGCC TTTAAACTAC CTATTGTTTT ATTTGAATTA TGAAGCTCTT GTGTTTATAT    14040

AAATTACAGT TAGGTACTGT GGAGACTAAT GGTAGCTACA ATAGTAATAT TAATAGCTAA    14100

AACTTAGTAG AATCTGATTG AGTTAATTTG GCCCTTTCCA TCATAAGGTA CTCTTCCCAA    14160

GCATCACATG ACCTGTGCTT AAGTCTGGTG GGGGCTTATG GCTTTGATAT TGAAAACAAA    14220

TCGTCAAGGA TGTTAATTTC TTGTTACTGC TATTACACTG AATTTTCTAT GGCTCTTTAG    14280

GAGAGGAAGA GACAAGTCTT CTTTTGGCAG GTGTTACTAA GTAGGCCATT TCCCAAGGAA    14340

CAGGGAATTT GCCAGGCTTT TGTGGTGGAG AGAATAGAAT GAATAAATGC TGTGGGGAGT    14400

AAAGAGCTTG TCAGAAGATG ATTAGTTCTG TGGCACCAAA ACCAAGAGAT CAGTTTTCCT    14460

GTGAGAAGTA AAGGAAGCAT TGTAGAAAAA TAGATGTGTT GAAGTCT                  14507
```

EXPRESSION AUGMENTING SEQUENCE ELEMENTS (EASE) FOR EUKARYOTIC EXPRESSION SYSTEMS

CROSS-REFERENCE TO RELATED APPLICATION

This application is a continuation of U.S. Ser. No. 08/785,150, filed Jan. 15, 1999, now U.S. Pat. No. 6,027,915 is a continuation-in-part of U.S. application Ser. No. 08/586,509, filed Jan. 11, 1996, now abandoned.

TECHNICAL FIELD OF THE INVENTION

The present invention relates to DNA sequence elements that augment the expression of recombinant proteins in eukaryotic cells.

BACKGROUND OF THE INVENTION

The development of expression systems for production of recombinant proteins is important for developing a source of a given protein for research or therapeutic use. Expression systems have been developed for both prokaryotic cells, such as *E. coli*, and for eukaryotic cells, which includes both yeast (i.e., Saccharonmices, Pichia and Kluyveromyces spp) and mammalian cells. Expression in mammalian cells is often preferred for manufacturing of therapeutic proteins, since post-translational modifications in such expression systems are more likely to resemble those found in a mammal than the type of post-translational modifications that occur in microbial (prokaryotic) expression systems.

Transcription of eukaryotic genes is regulated by a variety of cis- and trans-acting regulatory elements (reviewed by Dillon and Grosveld, *Trends Genet.* 9:134; 1993). Two of the best characterized cis elements are promoters and enhancers. Promoters are DNA sequences immediately 5' to the coding sequence of the gene and encompass multiple binding sites for trans-acting transcription factors, forming the basal transcription apparatus. Enhancers are also composed of multiple binding sites for trans-acting transcription factors but can be found far up stream or down stream of coding sequences or even within introns. These elements can also act in an orientation independent manner. The activities of promoters and enhancers can be detected in transient expression systems and contain elements which may or may not be tissue specific; they are vulnerable to position effects when studied in stable cell lines or transgenic animals.

Another category of cis- regulatory elements are ones which are believed to regulate the chromatin structure including, locus control regions (LCR) (Grosveld F., et al., *Cell* 51:975, 1987), matrix attachment regions (MAR; Phi-Van et al., *Mol Cell Biol* 10:2302; 1980), scaffold attachment regions (SAR; Gasser and Laemmli, *Trends Genet* 3:16, 1987), and insulator elements (Kellum and Schedl, *Cell* 64:941, 1991). These elements are similar to enhancers in that they are able to act over long distances, but are unique in that their effects are only detectable in stably transformed cell lines or transgenic animals. LCRs are also dissimilar to enhancers in that they are position and orientation dependent, and are active in a tissue specific manner. In addition, LCR and SAR sequences are characterized by A boxes, T boxes and topoisomerase II sites, which are not typically found in enhancer or promoter sequences. (Gasser and Laemmli, supra; Klehr D., et al., *Biochemistry* 30:1264, 1991).

Internal ribosome entry sites (IRES) are another type of regulatory element that can be found in several viruses and cellular RNAs (reviewed in McBratney et. al. *Current Opinion in Cell Biology* 5:961, 1993). IRES are useful in enhancing translation of a second gene product in a bicistronic eukaryotic expression cassette (Kaufman R. J., et al., *Nucleic Acids Res* 19:4485, 1991).

Several vectors are available for expression in mammalian hosts, each containing various combinations of cis- and in some cases trans- regulatory elements to achieve high levels of recombinant protein in a minimal time frame. However, despite the availability of numerous such vectors, the level of expression of a recombinant protein achieved in mammalian systems is often lower than that obtained with a microbial expression system. Moreover, developing a transformed cell line that expresses high levels of a desired protein often requires time consuming cloning and amplification. Accordingly, there is a need in the art to refine and improve expression in mammalian cells, and to identify elements that can augment expression of recombinant proteins and facilitate the use of mammalian cells in recombinant protein production.

SUMMARY OF THE INVENTION

Novel transcription regulatory sequences, expression augmenting sequence elements (EASE), that facilitate high expression of recombinant proteins in mammalian host cells in a short time period, are disclosed. One embodiment of the invention is an expression augmenting sequence element (EASE), that facilitates high expression of recombinant proteins in mammalian host cells in a short time period, which is not active in transient expression systems, does not exhibit characteristics of DNAs that encode a protein, and does not exhibit nucleotide sequence characteristics found in LCR, MAR or SAR. A preferred embodiment of the invention is an EASE that was obtained from Chinese hamster ovary (CHO) cell genomic DNA, proximal to a unique integration site for a recombinant mammalian protein.

In a most preferred embodiment of the invention, the EASE is selected from the group consisting of DNAs comprising nucleotides 1 through 14507, nucleotides 5980 through 14507, nucleotides 8671 through 14507, nucleotides 8671 through 10515, nucleotides 9277 through 10515, nucleotides 8672 through 12273, nucleotides 10100 through 14923 of SEQ ID NO:1, fragments of the foregoing DNAs that have expression augmenting activity, DNAs complementary to the foregoing DNAs, DNAs that are at least about 80% identical in nucleotide sequence to the foregoing DNAs and that have expression augmenting activity, and combinations of the foregoing DNAs that have expression augmenting activity. In one embodiment, the EASE DNA is ligated to a DNA comprising nucleotides 14290 through 14507 of SEQ ID NO:1; alternatively, the EASE DNA is ligated to a DNA comprising nucleotides 12592 through 14507 of SEQ ID NO:1.

Expression vectors comprising the novel EASE are able to transform CHO cells to high expression of recombinant proteins. Thus, another embodiment of the invention is an expression vector comprising an EASE. In a preferred embodiment, the expression vector further comprises a eukaryotic promoter/enhancer driving the expression of a protein of interest. In a most preferred embodiment, the expression vector consists of a bicistronic plasmid wherein a first exon encodes the gene of interest and a second exon encodes an amplifyable dominant selectable marker. A preferred marker is dihydrofolate reductase (DHFR); other amplifyable markers are also suitable for use in the inventive expression vectors. The expression vector may further comprise an IRES sequence between the two exons.

Mammalian host cells can be transformed with the inventive expression vectors, and will produce high levels of recombinant protein in a short period of time. Accordingly, another embodiment of the invention provides a mammalian host cell transformed with the inventive expression vector. In a most preferred embodiment, the host cells are CHO cells.

The invention also provides a method for obtaining a recombinant protein, comprising transforming a host cell with an inventive expression vector, culturing the transformed host cell under conditions promoting expression of the protein, and recovering the protein. In a preferred application of this invention, transformed host cell lines are selected with two selection steps, the first to select for cells expressing the dominant amplifyable marker, and the second step for high expression levels and/or amplification of the marker gene as well as the gene of interest. In a most preferred embodiment, the selection or amplification agent is methotrexate, an inhibitor of DHFR that has been shown to cause amplification of endogenous DHFR genes and transfected DHFR sequences.

Moreover, the invention provides a method of identifying additional expression augmenting sequence elements, for example, from other transformed cell lines. Such cell lines will exhibit high levels of expression that are not attributable to high gene copy number. The inventive techniques will be useful in identifying and isolating such EASE, as well as EASE present in non-transformed cells (for example, by hybridization studies or sequence analysis).

BRIEF DESCRIPTION OF THE DRAWINGS

FIGS. 1A and 1B present inserts of various lengths, derived from 2A5-3 CHO genomic DNA. FIG. 1B summarizes inserts cloned into pGEM1, derived from the phage clone represented in FIG. 1A, as described in Example 7. The thick black line is the CMV promoter, the dotted box is the adenovirus tripartite leader sequence, the left hatched boxes are the TNFrFc coding region and the smaller hatching is the DHFR-encodinc sequence. Relative to SEQ ID NO:1, the insert in PG8.5 corresponds to nucleotides 5980 through 14507; that in PG5.7 corresponds to nucleotides 8671 through 14507; that in PG5.7AS corresponds to nucleotides 8671 through 10515 ligated to nuclcotides 12592 through 14507; that in PG.2SE1.8 corresponds to nucleotides 8671 through 10515 ligated to nucleotides 14290 through 14507; that in PG.2SH1.2 corresponds to nucleotides 9277 through 10515 ligated to nucleotides 14291 through 14507; that in PG.2.2 corresponds to nucleotides 12269 through 14507; and the insert in PG.2 corresponds to nucleotides 14290 through 14507.

DETAILED DESCRIPTION OF THE INVENTION

We have isolated and identified novel sequence elements that can improve expression of reporter proteins two to eight fold in stable cell pools when inserted in an expression vector. One such sequence element was identified by cloning the integration site of a unique expression cassette encoding recombinant dimeric Tumor Necrosis Factor receptor/immunoglobulin Fc fusion protein (TNFrFc) from genomic DNA of a cell line expressing this protein at a high level. The inventive sequence elements appear to encode a novel function, since the expression enhancing activity does not behave like previously characterized cis-acting elements such as promoters, enhancers, locus control regions, scaffold attachment regions or matrix attachment regions. In addition the sequence elements do not appear to contain any open reading frames (ORFs), making it unlikely that they encode a novel trans-activator protein. We refer to these novel sequence elements as "expression augmenting sequence elements" (EASE).

Physical and Functional Characterization of EASE

EASE activity was identified in 14.5 kb of CHO genormic DNA 5' to a unique integration site of TNFrFc encoding sequences from the genome of a cell line expressing this protein at a high level (referred to as 2A5-3). Expression vectors containing this isolated, 14.5 kb region and shorter fragments thereof were able to transform DXB11 CHO cells to high levels of expression of recombinant proteins at a frequency of >50%. Mapping studies indicated that >50% of the activity is located in a 1.8 kb region of the DNA, from nucleotide 8671 to nucleotide 10515 of SEQ ID NO:1. In addition, a sequence nucleotide 8671 to nucleotide 9276 of SEQ ID NO:1 (the 604 bp Ecor1 to Hpa1 fragment) appears to be essential for activity, as expression enhancement is greatly reduced if this region is not present in a vector. The inventive EASE may improve expression of a recombinant protein driven by a promoter/enhancer region to which it is linked.

Moreover, additional fragments of the 14.5 kb of CHO genomic DNA exhibiting EASE activity can be identified as described herein, as can similar EASE motifs from other types of cells or from other integration sites in transformed cells. In addition, it is known in the art that subsequent processing of fragments of DNA prepared by restriction enzyme digestion can result in the removal of additional nucleotides from the ends of the fragments. Thus, the DNA fragments described and claimed herein also include fragments that end within five base pairs of the nucleotides listed.

Other combinations of the fragments described herein can also be developed, for example, sequences that included multiple copies of the EASE disclosed herein, or sequences derived by combining the disclosed EASE with other nucleotide sequences to achieve optimal combinations of regulatory elements. Such combinations can be contiguously linked or arranged to provide optimal spacing of the EASE fragments (i.e., by the introduction of 'spacer' nucleotides between the elements). Regulatory elements can also be arranged to provide optimal spacing of the EASE from other regulatory regions. Similarly, the orientation of an EASE in a vector can be optimized to provide high levels of protein expression.

The EASE disclosed herein was isolated from Chinese hamster ovary (CHO) cells. Homologous expression augmenting elements are expected to exist in cells from other mammalian species as well as in cell lines derived from other tissue types, and can be isolated by techniques that are well-known in the art, for example by cross-species hybridization or PCR-based techniques. In addition, changes can be made in the nucleotide sequence set forth in SEQ ID NO:1 by site-directed or random mutagenesis techniques that are known in the art. The resulting EASE variants can then be tested for EASE activity as described herein. DNAs that are at least about 80% identical, more preferably at least about 90% identical, in nucleotide sequence to SEQ ID NO:1 or fragments thereof having EASE activity are isolatable by routine experimentation, and expected to have EASE activity. For fragments of EASE, percent identity refers to that portion of the reference native sequence that is found in the EASE fragment. Accordingly, homologs of EASE and variants of EASE are also encompassed by the invention.

The expression of recombinant proteins is driven by an appropriate eukaryotic promoter/enhancer and the inventive EASE. Cells are transfected with a plasmid selected under low stringency for the dominant selectable marker and then selected again in higher stringency, for example, by using methotrexate (MTX), an inhibitor of DHFR in the selection media. The first selection yields positive transformants (i.e., DHFR$^+$ transformants in the case of methotrexate selection), and the second selection yields transformants which express high levels of the gene of interest.

Inclusion of an IRES sequence into vectors containing an EASE may be beneficial for enhancing expression of some proteins. The IRES sequence appears to stabilize expression of the gene of interest under high selective pressure (Kaufman et al. 1991, supra). For proteins which are processed well by the cells, the IRES sequence is not necessary to achieve high expression levels.

Cell populations expressing high levels of recombinant protein can be developed in five to seven weeks using a two step selection protocol as described herein. The absolute level of high expression will vary with the specific protein, depending on how well the protein is processed by the cell. We have observed stable cell pools expressing at least about $0.2 \mu g/10^6$ cells/day, and in many cases greater than about 12 $\mu g/10^6$ cells/day, using a variety of cytokines and cytokine receptors. The time required to achieve this level of protein expression was almost half that observed for similar transformations done using vectors without EASE. Moreover, cell pools developed with EASE are stable over time, and can be treated as cell lines for most purposes. Cloning steps can be delayed until later in the process of development than is customary for recombinant proteins. With an additional cloning step, it is possible to develop cell lines expressing greater than about 24 $\mu g/10^6$ cells/day.

Transfection experiments demonstrate that EASE found in these DNA sequences have some characteristics of previously described cis-acting elements but do not fall into previously described definitions. Similar to LCR, MAR and SAR sequences, EASE activity is not detected in transient assays. Unlike these sequences however, EASE does not have A boxes, T boxes or topoisomerase 2 sites typically found in these elements (Klehr et al., supra). Since EASE activity is not detected in transient assays, they also appear to be distinct from promoter and enhancer elements, which arc detected with these methods.

Expression of Recombinant Proteins

Recombinant expression vectors include synthetic or cDNA-derived DNA fragments encoding the protein, operably linked to suitable transcriptional or translational regulatory elements derived from mammalian, viral or insect genes. Such regulatory elements include a transcriptional promoter, a sequence encoding suitable mRNA ribosomal binding sites, and sequences which control the termination of transcription and translation, as described in detail below. Mammalian expression vectors may also comprise nontranscribed elements such as an origin of replication, a suitable promoter and enhancer linked to the gene to be expressed, other 5' or 3' flanking nontranscribed sequences, 5' or 3' nontranslated sequences such as necessary ribosome binding sites, a polyadenylation site, splice donor and acceptor sites, and transcriptional termination sequences. An origin of replication that confers the ability to replicate in a host, and a selectable gene to facilitate recognition of transformants, may also be incorporated.

DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading frame.

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. Viral genomic promoters, control and/or signal sequences may be utilized to drive expression. provided such control sequences are compatible with the host cell chosen. Exemplary vectors can be constructed as disclosed by Okayama and Berg (*Mol. Cell. Biol.* 3:280, 1983). Non-viral cellular promoters can also be used (i.e., the β-globin and the EF-1α promoters), depending on the cell type in which the recombinant protein is to be expressed.

DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al., *Nature* 273:113, 1978). Smaller or larger SV40 fragments may also be used, provided the approximately 250 bp sequence extending from the Hind III site toward the BglI site located in the viral origin of replication is included.

Bicistronic expression vectors used for the expression of multiple transcripts have been described previously (Kim S. K. and Wold B. J., *Cell* 42:129, 1985; Kaufman et al. 1991, supra). pCAVDHFR is a derivative of pCD302 (Mosley et al Cell 1989) containing the coding sequence for mouse DHFR (Subramani et al., *Mol. Cell. Biol.* 1:854, 1981). The pCDE vector is a derivative of pCAVDHFR containing the murine encephalomyocarditis virus internal ribosomal entry site (nucleotides 260 through 824; Jang and Wimmer, *Genes and Dev.* 4:1560, 1990) cloned between the adenovirus tripartite leader and the DHFR cDNA coding sequence. Other types of expression vectors will also be useful in combination with the inventive EASE, for example, those described in U.S. Pat. Nos. 4,634,665 (Axel et al.) and 4,656,134 (Ringold et al.).

Host Cells

Transformed host cells are cells which have been transformed or transfected with expression vectors constructed using recombinant DNA techniques and which contain sequences encoding recombinant proteins. Expressed proteins will preferably be secreted into the culture supernatant, depending on the DNA selected, but may be deposited in the cell membrane. Various mammalian cell culture systems can be employed to express recombinant protein. Examples of suitable mammalian host cell lines include the COS-7 lines of monkey kidney cells, described by Gluzman (*Cell* 23:175, 1981), and other cell lines capable of expressing an appropriate vector including, for example, CV-1/EBNA (ATCC CRL 10478), L cells, C127, 3T3, Chinese hamster ovary (CHO), HeLa and BHK cell lines.

A commonly used cell line is DHFR⁻ CHO cells which are auxotrophic for glycine, thymidine and hypoxanthine, and can be transformed to the DHFR⁺ phenotype using DHFR cDNA as an amplifyable dominant marker. One such DHFR⁻ CHO cell line, DXB11, was described by Urlaub and Chasin (*Proc. Natl. Acad. Sci. USA* 77:4216, 1980). Other cell lines developed for specific selection or amplification schemes will also be useful with the inventive EASE.

Preparation of Transformed Mammalian Cells

Several transformation protocols are known in the art, and are reviewed in Kaufman, R. J., *Meth. Enzymology* 185:537 (1988). The transformation protocol chosen will depend on the host cell type and the nature of the gene of interest, and can be chosen based upon routine experimentation. The basic requirements of any such protocol are first to introduce DNA encoding the protein of interest into a suitable host cell, and then to identify and isolate host cells which have incorporated the heterologous DNA in a stable, expressible manner.

One commonly used method of introducing heterologous DNA is calcium phosphate precipitation, for example, as described by Wigler et al. (*Proc. Natl. Acad. Sci. USA* 77:3567, 1980). DNA introduced into a host cell by this method frequently undergoes rearrangement, making this procedure useful for cotransfection of independent genes.

Polyethylene-induced fusion of bacterial protoplasts with mammalian cells (Schaffner et al., *Proc. Natl. Acad. Sci. USA* 77:2163, 1980) is another useful method of introducing heterologous DNA. Protoplast fusion protocols frequently yield multiple copies of the plasmid DNA integrated into the mammalian host cell genome; however, this technique requires the selection and amplification marker to be on the same plastmid as the gene of interest.

Electroporation can also be used to introduce DNA directly into the cytoplasm of a host cell, for example, as described by Potter et al. (*Proc. Natl. Acad. Sci. USA* 81:7161, 1988) or Shigekawa and Dower (*BioTechiniques* 6:742, 1988). Unlike protoplast fusion, electroporation does not require the selection marker and the gene of interest to be on the same plasmid.

More recently, several reagents useful for introducing heterologous DNA into a mammalian cell have been described. These include Lipofectin® Reagent and Lipofectamine™ Reagent (Gibco BRL, Gaithersburg, Md.). Both of these reagents are commercially available reagents used to form lipid-nucleic acid complexes (or liposomes) which, when applied to cultured cells, facilitate uptake of the nucleic acid into the cells.

A method of amplifying the gene of interest is also desirable for expression of the recombinant protein, and typically involves the use of a selection marker (reviewed in Kaufman, R. J., supra). Resistance to cytotoxic drugs is the characteristic most frequently used as a selection marker, and can be the result of either a dominant trait (i.e., can be used independent of host cell type) or a recessive trait (i.e., useful in particular host cell types that are deficient in whatever activity is being selected for). Several amplifyable markers are suitable for use in the inventive expression vectors (for example, as described in Maniatis, *Molecular Biology: A Laboratory Manual*, Cold Spring Harbor Laboratory, N.Y., 1989; pgs 16.9–16.14).

Useful selectable markers for gene amplification in drug-resistant mammalian cells are shown in Table 1 of Kaufman, R. J., supra, and include DHFR-MTX resistance, P-glycoprotein and multiple drug resistance (MDR)-various lipophilic cytoxic agents (i.e., adriamycin, colchicine, vincristine), and adenosine deaminase (ADA)-Xyl-A or adenosine and 2'-deoxycoformycin.

Other dominant selectable markers include microbially derived antibiotic resistance genes, for example neomycin, kanamycin or hygromycin resistance. However, these selection markers have not been shown to be amplifyable (Kaufman, R. J., supra,). Several suitable selection systems exist for mammalian hosts (Maniatis supra, pgs 16.9–16.15. Co-transfection protocols employing two dominant selectable markers have also been described (Okayama and Berg, *Mol. Cell Biol* 5:1136, 1985).

A particularly useful selection and amplification scheme utilizes DHFR-MTX resistance. MTX is an inhibitor of DHFR that has been shown to cause amplification of endogenous DHFR genes (Alt F. W., et al., *Journal of Biological Chemistry* 253:1357, 1978) and transfected DHFR sequences (Wigler M., et al., *Proc. Natl. Acad. Sci. USA* 77:3567, 1980). Cells are transformed with DNA containing the gene of interest in one expression cassette, linked or unlinked to the DHFR gene in a second expression cassette. The two genes can also be in one bicistronic expression unit (Kaufman et al., 1991 supra and Kaufman R. J., et al., *EMBO J* 6:187, 1987). Transformed cells are grown in media containing successively greater amounts of MTX, resulting in greater expression of the DHFR gene, as well as the gene of interest.

Useful regulatory elements. described previously, can also be included in the plasmids used to transform mammalian cells. The transformation protocol chosen, and the elements selected for use therein, will depend on the type of host cell used. Those of skill in the art are aware of numerous different protocol and host cells, and can select an appropriate system for expression of a desired protein, based on the requirements of their cell culture systems.

The relevant disclosures of all references cited herein are specifically incorporated by reference. The following examples are intended to illustrate particular embodiments, and not limit the scope, of the invention.

EXAMPLES

Example 1

Genomic Library Screening and Subcloning

A transformed CHO cell line (designated the 2A5-3 cell line) expressing high levels of an immunoglobulin Fc fusion protein comprising the extra cellular domain of the 80 Kd receptor for Tumor Necrosis Factor (TNFrFc; Mohler et al., *J. Immunol.* 151:1548, 1993; U.S. Pat. No. 5,395,760, issued Mar. 7, 1995; the disclosure of both of which are incorporated by reference) was selected for preparation of a genomic library since Southern blot analysis indicated that the high expression of TNFrFc expression observed for this cell line is driven by a single integration of an expression cassette encoding TNFrFc. DNA was isolated from these cells, partially digested with Mbo1 and cloned into a lambda FIX II cloning vector (Stratagene custom genonic library; Stratagene La Jolla, Calif.) to form a library. The p80 TNF receptor coding sequence, along with 14.4 kb of cellular flanking sequences, was cloned from the library as described below.

To screen the library; approximately $2 \times 10^4$ plaque forming units (pfu) were allowed to form per 250 cm plate. Plaques were transferred to nitrocellulose membranes (Schleicher and Schuell, Keene, N.H.) and lysed using standard protocols supplied by Stratagene. The filters were probed with random primed Not1 PvuII DNA fragment encoding a cell surface portion of p80 TNF receptor extracellular domain (Mohler et al. supra). Hybridizations were performed at 63° C. in hybridization buffer [(10×Denharts solution (Maniatis supra, pg. 9.49), 0.05M Tris pH 7.5, 1M NaCl, 0.1% sodium pyrophosphate, 1% SDS, 4 µg/ml salmon sperm DNA]. Filters were washed as follows: initial wash in 0.1% SDS, 0.1% SSC (Maniatis supra, B.13) at 42° C. for 30 min., followed by two additional washes in the same solution for 60 min. at 63° C. The final two washes were at 63° C. for 60 min. using 0.1% SDS and 0.01% SSC. A single positive recombinant clone was identified after screening about 4×10$^5$ recombinants. This clone, which was designated 2A5-3 λ, was used in all subsequent analyses. The nucleotide sequence of the CHO genomic DNA from this clone is shown in SEQ ID NO:1. The 2A5-3 λ was deposited with the American Type Culture Collection, Rockville Md., under the terms of the Budapest Treaty on Jan. 4, 1996, and given accession number 97411.

Example 2

Southern Blotting

Gene copy number was monitored using Southern blot technique. Total cellular DNA from the appropriate cell lines was prepared using previously described methods (Mitchell P. J., et al., *Mol Cell Biol* 6:425, 1986). After digestion of DNA with appropriate enzymes in conditions described by the suppliers (New England Biolabs, Beverly, Mass. or Bochringer Mannheim, Indianapolis, Ind.), DNA is run on 1% TAE (Tris-acetate buffered) agarose gels, for example as described (Maniatis supra, pg. 6.20). After electrophoresis, DNA is transferred to Zetaprobe filters and hybridized in conditions recommended by the supplier (Bio-Rad Laboratories, Richmond, Calif.). Filters are washed with 0.1% SDS and 0.1×SSC three times for 30 minutes each. The first wash was performed at 37° C. and the two subsequent washes were done at 63° C. Probes were prepared using random priming kits (Boehringer Mannheim, Indianapolis, Ind.). For blots, TNFr sequences were detected using the same probe as described for the library screen. Similarly, probes derived from the region of DNA encoding any other protein of interest (or fragment thereof) will be useful in a Southern blot technique to monitor gene copy number.

Example 3

Tissue Culture

Dihydrofolate reductase (DHFR) deficient Chinese hamster ovary (CHO) cells DXB11 (Chasin and Urlaub, supra) cells were maintained in Dulbecco's minimal essential medium and F12 (DMEM:F12) supplemented with 7.5% fetal bovine serum (FBS; Hyclone, Logan, Utah; or Sigma, St. Louis, Mo.), 2 mM L-glutantine, 90 µM thynidine (T), 90 µM hypoxanthine (H) and 120 µM glycine (G). For DHFR selection studies and methotrexate selections, cells were cultured in DMEM:F12 lacking GHT and supplemented with 7.5% dialyzed FBS, 6 mM L-glutarnine and 1 mM asparagine. For methotrexate selections, methotrexate (MTX; Lederle Laboratories, Pearl River, N.Y.) was added to the selection media at appropriate concentrations. When neomycin selection was employed, 400 µg/ml of G418 (Gibco, Grand Island, N.Y.) was added to the media. The cells were transfected using calcium phosphate transfection (Wigler et al. supra), or Lipofectamine™ transfection as recommended by the supplier (Gibco BRL, Gaithersburg, Md.).

Example 4

Enzyme Linked Immunosorbent Assays (ELISA)

Production of recombinant proteins can be monitored by any assay suitable for detecting the desired protein, including binding assays, inhibition assays, and biological assays. A particularly useful assay is the antibody sandwich enzyme-linked immunosorbent assay (ELISA), which is well known in the art (for example, adaptations of the techniques disclosed in Engvall et al., *Immunochem.* 8:871, 1971 and in U.S. Pat. No. 4,703,004). In this assay, a first antibody specific for a protein of interest (usually a monoclonal antibody) is immobilized on a substrate (most often, a 96-well microtiter plate), then a sample containing the protein is added and incubated. A series of dilutions of a known concentration of the protein is also added and incubated, to yield a standard curve. After a wash step to remove unbound proteins and other materials, a second antibody to the protein is added. The second antibody is directed against a different epitope of the protein, and may be either a monoclonal antibody or a polyclonal antibody.

A conjugate reagent comprising an antibody that binds to the second antibody conjugated to an enzyme such as horse radish peroxidase (HRP) is added, either after a second wash step to remove unbound protein, or at the same time the second antibody is added. Following a suitable incubation period, unbound conjugate reagent is removed by washing, and a developing solution containing the substrate for the enzyme conjugate is added to the plate, causing color to develop. The optical density readings at the correct wavelength give numerical values for each well. The values for the sample are compared with the standard curve values, permitting levels of the desired protein to be quantitated.

To quantitate trimeric CD40 ligand, a CD40L ELISA using two monoclonal antibodies (MAb) was developed. One antibody was directed against an oligomerizing zipper domain present in the trimeric protein, and the second antibody was directed against the human CD40 ligand portion of the molecule. The first MAb was adsorbed onto plates overnight, and the peroxidase (HRP) conjugated second antibody was added after a wash step. In several experiments quantities of between 0.78 and 50 ng/ml CD40L were detected.

A similar ELISA was used to quantitate recombinant human tumor necrosis factor receptor fusion protein (TNFrFc). In this ELISA two monoclonal antibodies against different epitopes of TNFrFc were used. Again, the first MAb was adsorbed onto plates overnight, and the peroxidase (HRP) conjugated second antibody was added after a wash step. In several experiments quantities of between 0.78 and 50 ng/ml TNFrFc were detected.

For detecting recombinant Flt-3 ligand (Flt-3L), a somewhat different ELISA as used, employing a monoclonal antibody and a rabbit polyclonal antiserum. As described previously, the MAb was adsorbed onto plates overnight. A solution containing both the polyclonal anti-Flt-3L and the peroxidase (HRP)-conjugated second antibody (donkey anti-rabbit immunoglobulin) was added after the first wash step to remove unbound proteins. In several experiments quantities of between 1.56 and 100 ng/ml Flt-3L were detected.

Example 5

Sequencing and Data Base Searches

DNA was sequenced using shotgun sequencing as described previously (Bankier, *Meth Mol Biol* 23:47, 1993) or primer walking using the ABI Taq DyeDeoxy Terminator Cycle Sequencing kit on an automated DNA sequencer (model 373a; Applied Biosystems, Foster City, Calif.). The 2A5-3 λ DNA was characterized by performing several different type of computer analysis.

(a) Compositional Analysis

The 2A5-3 λ sequence was scanned for regions of high A+T content using a combination of the three computer programs available from the Wisconsin Package from the Genetics Computer Group (Program Manual for the Wisconsin Package, Version 8, September 1994, Genetics Computer Group, 575 Science Drive, Madison, Wis., USA 53711), namely SIMPLIFY, WINDOW, and STATPLOT. To search for regions of high A+T content, a sliding window of 50 base pairs was slid across the 2A5-3 λ sequence in one base-pair increments, and the percentage A+T within that window was plotted. Areas of interest were those where the average A+T content was consistently above 70 percent. One region with >200 base pairs of with >70% A+T content was found between the two SwaI sites (nucleotides 10517 through 12591 of SEQ ID NO:1). This region did not appear to be important for EASE activity (see examples 7 and 8).

(b) Transcription Enhancement Motifs

A search was performed for three known transcription-enhancing motifs using the GCG program MOTIFS: "Topo-II" [GTNWAYATTNATNNR], "T-box" [ATATTT/AATATT], and "A-box" [AATAAAYAAA] (Klehr et al. supra). This program scans a query sequence in a linear fashion looking for an exact match to each specified input motif. For each motif, degeneracies were designated with symbols using the naming conventions of the International Union of Biochemistry (IUB). No "topo-II boxes" were found in the 14.5 kb of CHO DNA in the 2A5-3 λ DNA. Two "A-boxes" and 26 "T-boxes" were found dispersed throughout this region of CHO DNA. None of these motifs were found in the 604 bp Ecor1 to Hpa1 fragment required for EASE activity.

(c) Sequence Database Search for Similarity

Database searches of the GenBank DNA sequence databases and the SwissProt and PIR protein sequence databases were performed using the BLAST algorithm of Altschul et al. (*J. Mol. Biol.* 215:403; 1990). This algorithm is optimized for finding segments of local similarity without inserting gaps in the alignment. BLAST searches on both the 2A5-3 λ DNA sequence and a dynamic protein translation in all six reading frames failed to produce significant matches with any known transcriptional activation sequences.

(d) Coding Sequence Analysis

The computer program GRAIL (Uberbacher, E. C., and Mural, R. J., *Proc. Natl. Acad. Sci. USA* 88:11261; 1991), a neural-network based gene-recognition system was used to scan the 2A5-3 λ sequence for potential coding regions. A GRAIL search evaluates the coding potential of a DNA sequence within a sliding 100 bp window. To avoid bias, searches for potential coding regions were performed both with and without respect to additional genomic features (e.g., splice junctions and translation starts). The results of GRAIL searches did not indicate any regions of high protein coding potential within the 2A5-3 λ sequence.

Example 6
Expression of Proteins Using the Cloned Sequences

The purpose of this experiment was to determine if the sequences surrounding the TNFrFc integration site in CHO cell line 2A5-3 could confer high expression of this protein when randomly integrated into DXB 11 cells. This integration site was cloned as described in Example 1, and DXB11 CHO cells were co-transfected with either 5 μg of 2A5-3 λ DNA or 5 μg of a control plasmid, and 1 μg of pSV3NEO (this expression vector contains the G418 resistance marker gene driven by the SV40 promoter) DNA using calcium phosphate transformation. Control cells were transformed with an expression vector for TNFrFc called pCAVDHFRp80 consisting of the CMV promoter/enhancer driving expression of a bicistronic message where the first intron is sequence encoding TNFrFc and the second intron encodes murine DHFR. pCAVDHFRp80 is the plasmid that was used to construct the 2A5-3 cell line. After a 48 hr. recovery period cells were split 1:3 or 1:2 into 10 cm dishes in media containing 400 μg/ml G418. After a seven to nine day selection in G418-containing medium, resistant colonies were detected and 24 pools consisting of one to three colonies were selected and seeded into 24 well plates.

When the cells reached confluence, the medium was changed to medium lacking GHT to select for DHFR+ cells. Eight of the doubly selected pools were assayed for specific productivity of TNFrFc by ELISA as described in Example 5, and it was found that 40% of the pools had expression levels 75% or greater than that of the parental cell line (see Table 1 below).

TABLE 1

Specific Production of TNFrFc
by Cells Transformed with 2A5-3 λDNA

| Cell line or pool* | $\mu g/10^6$ cells/day |
|---|---|
| 1. 2A5-3 | 2.88 |
| 2. 2A5-3.3 | 3.40 |
| 3. 2A5-3.6 | 1.45 |
| 4. 2A5-3.8 | 1.17 |
| 5. 2A5-3.10 | 0.04 |
| 6. 2A5-3.11 | 1.16 |
| 7. 2A5-3.13 | 1.99 |
| 8. 2A5-3.15 | 2.40 |
| 9. 9A5-3.24 | 4.00 |
| 10. p80.8 | BR** |
| 11. p80.9 | 0.01 |
| 12. p80.20 | 0.02 |

*1: parental cell line(positive control);
2–9: cell pools transformed with 2A5-3 λ;
10–12: cell pools transformed with CAVDHFRTNFrp80 (negative control)
**BR: below range Three of these pools were monitored over 10 passages and it was found that expression remained greater than or equal to that of the parental cell line, as shown in the Table 2 below.

TABLE 2

Specific Production of TNFrFc by Cells
Transfected with 2A5-3 λDNA, Multiple Passages

| Cells | passage # | $\mu g/10^6$ cells/day |
|---|---|---|
| 2A5-3 parental cell line | 75 | 1.59 |
|  | 83 | 1.30 |
| 2A5-3.8 pool | 3 | 2.75 |
|  | 11 | 1.46 |
| 2A5-3.13 pool | 3 | 2.55 |
|  | 11 | 1.91 |
| 2A5-3.13 pool | 3 | 4.17 |
|  | 11 | 2.65 |

This experiment was repeated by doing a second co-transfection, and similar results were obtained. In both co-transfection experiments, a decrease in specific production as the pools were passaged was observed, most likely due to the fact that, in the mixed cell population of the pools, faster growing cells that produced lower amounts of recombinant protein outgrew the slower growing, higher producing cells. Even with the decrease in specific production, all cell pools maintained production levels greater than that or equal to that of the parental cell line. The results indicated that the 2A5-3 λ DNA insert can confer expression of an indicator protein near that of the parental cell line at a high frequency (≧40%) when randomly integrated into DXB11 CHO cell DNA.

Example 7
Identification of Fragments Having EASE Activity

Figure 1A:
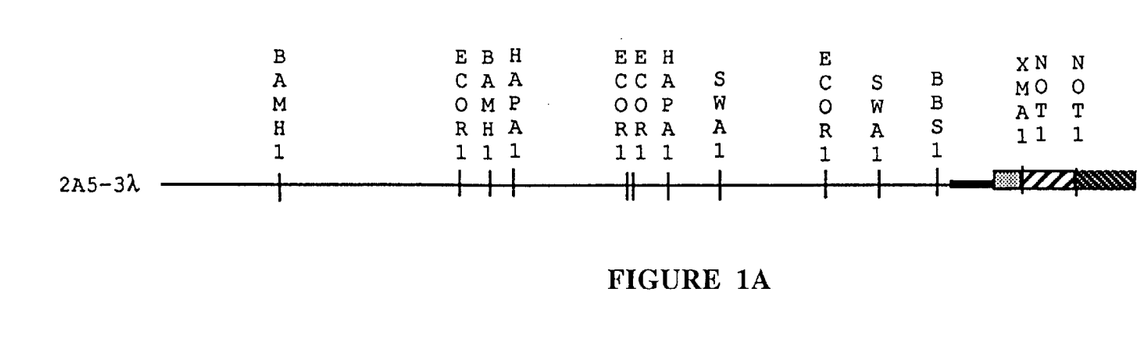
FIG. 1A is a restriction map of the TNFrFc integration site cloned into a cloning vector, λFixII, as described in Example 1; restriction sites used for subcloning are indicated. The insert corresponds to nucleotides 1 through 14507 of SEQ ID NO:1.

In a second series of co-transfection experiments, it was determined that shorter segments of 2A5-3 λ DNA could confer high expression of recombinant proteins, but with lower frequency than 2A5-3 λ. Various portions of the phase insert were subcloned into bluescriptII (Stratecene, La Jolla, Calif.), or pGEM-11Zf(-) (Promega, Madison, Wis.) for sequencing and restriction mapping, using standard techniques of restriction enzyme cutting and liation (see FIG. 1). For protein expression studies, various inserts were derived from thic phlae clone shown in FIG. 1A, and Subcloned into pGEM1 (Promega, Madison, Wis.). Restriction sites used for subcloning are indicated in the restriction map presented in FIG. 1A.

DXB11CHO cells were transfected with 0.2 μg TNFrFc encoding sequences for each TNFrFc expression plasmid and 0.1 μg of pSV3neo using the Lipofectamine™ reagent (Gibco BRL, Gaithersburg, Md.). After a 48 hour period, the cells were split 1:4 or 1:40 into G418 selective media. Colonies were visible in a 7–10 day time period, at which point the media was changed to -H or -GHT DHFR selective media. After selection for 10–13 days in DHFR selective media, pools of 1–3 colonies were picked and plated in 24 well vessels. The cultures were sampled at confluence and frequency of high expression was scored (see Table 3). It was found that high expression could be achieved with vectors containing at a minimum an Ecor1 to Swal 2.8 kb fragment 3.9 kb from the CMV promoter and a 1.9 kb sequence immediately 5' of the CMV promoter (PG5.7ΔS). Plasmids containing larger amounts of insert (PG8.5 and PG5.7) were also effective at enhancing expression.

TABLE 3

Percent of Pools Expressing >0.5 μg/ml Recombinant Protein

| | Recombinant Protein: | | | |
| --- | --- | --- | --- | --- |
| | HuTNRrFc | | HuFlt-3L | |
| Construct: | exp't 1 | exp't 2 | exp't 1 | exp't 2 |
| 2A5-3 λ | 100 (n = 8) | 100 (n = 6) | na | na |
| PG8.5 | 70 (n = 19) | 100 (n = 11) | na | na |
| PG5.7 | 40 (n = 14) | 100 (n = 13) | 100 (n = 12) | 80 (n = 12) |
| PG5.7ΔS | 100 (n = 12) | 50 (n = 10) | na | 50 (n = 6) |
| PG.2SE1.8 | na1 | 100 (n = 12) | na | na |
| PG.2SH1.2 | na | 0.0 (n = 12) | na | na |
| PG2.2 | 0 (n = 12) | 0.0 (n = 12) | na | 0.0 (n = 12) |
| PG.2 | na | 0.0 (n = 12) | na | na |

1: not assayed

A similar set of expression plasmids comprising DNA encoding the extracellular portion of Flt-3 lingand (Lynman et al., *Blood* 91:2795, 1994 and U.S. Ser. No. 08/242,545, filed May 11, 1994) was prepared and tested as described above. As was observed for TNFrFc, high levels of expression could be achieved with the PG5.7ΔS vector but not the PG2.2 vector or the PG.2 vector. The results of these experiments indicated that the high frequency of high recombinant protein expression is not protein specific and that the 1.8 kb Ecor1 to Swa1 band is essential for this activity.

Additional fragments were prepared and tested for expression augmenting activity. Construct PG3.6 comprised an EcorI fragment, represented by nucleotides 8672 through 12273 of SEQ ID NO:1; it was ligated to nucleotides 14290 through 14507 in a manner similar to constructs PG.2SE1.8 and PG.2SH1.2. A similar construct was also prepared from a BbsI fragment represented by nucleotides 10100 through 14293 of SEQ ID NO:1. Both of these constructs showed expression augmenting activity, which was comparable to that of construct PG5.7. A construct, referred to as PG3.8, consisting of a BamII fragment (nucleotides 2221–5984) ligated to nucleotides 14290 through 14507 of SEQ ID NO:1 did not exhibit activity.

Figure 1B:
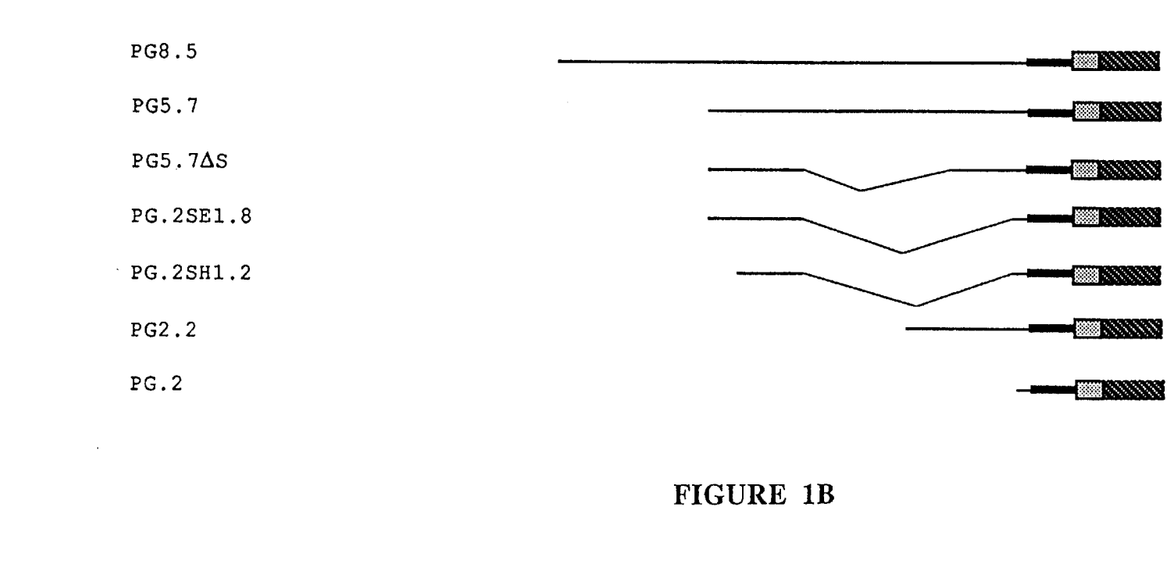

The results of these experiments indicated that the region of the 2A5-3 λ DNA that exhibits expression augmenting activity lies primarily between nucleotides 5980 (the BamHI site in FIG. 1) and 14290 (the BbsI site on FIG. 1). Further experiments using the SV40 promotor/enhancer demonstrated that expression augmenting activity was not promotor dependent. Additionally, EASE-containing constructs were also successfully introduced into cells by electroporation, and exhibited expression augmenting activity. However, expression augmenting activity was not observed when EASE-containing, constructs were transfected into a monkey cell line (Vero), indicating the possibility of either species or cell type specificity for the EASE of SEQ ID NO:1.

Example 8
Comparising Specific Productivity

To more accurately quantitate the expression from clones transfected with plasmids containing shorter lengths of integation site DNA and compare it to clones derived from transfection with the phage DNA, the specific productivity of the three highest expressing pools transformed with the PG5.7ΔSTNFrFc construct and the three highest expressing pools transformed with the phage DNA were compared (Table 4). In this experiment it was found that the expression level for all six pools was not significantly different when compared using standard T test (p=0.14).

TABLE 4

Comparative expression of recombinant protein expressed using Phage DNA or PG5.7dS

| Cell pool | Average μg/10⁶ cells/day¹ |
| --- | --- |
| 2a5.3.3 | 3.06 ± 0.60 |
| 2a5.3.7 | 2.67 ± 0.28 |
| 2a5.3.11 | 3.37 ± 0.54 |
| PG5.7ΔS.1 | 2.25 ± 0.35 |
| PG5.7ΔS.4 | 2.79 ± 0.89 |
| PG5.7ΔS.6 | 2.65 ± 0.34 |

1: n = 2

These results, taken together with the frequency data shown in Table 3, indicates that the PG5.7ΔS vector contains all the sequence information necessary for high level expression.

Example 9
Characterization of the EASE

To further characterize the expression enhancing activity found in the 2A5-3 λ-derived expression vectors, a colony forming assay was performed. Here, 0. 16 μg DHFR encoding sequences from plasmids PG8.5, PG5.7ΔS, PG.2SE1.8, PG.2SH1.2 and PG.2 were transfected into DXB11 cells using Lipofectamine™. After a 48 hour expression period cells were plated at 1×10⁴ cells/plate in -GHT medium containing various concentrations of MTX. After nine to eleven days, the plates were fixed with methanol and stained with methylene blue for colony formation. Greater colony formation was detected with plasmids PG8.5, PG5.7ΔS, and PG.2SE1.8 compared with plasmids PG.2SH1.2 and PG.2 plasmid at 0 nM and 10 nM MTX (See table 5).

TABLE 5

Colony formation using pgem vectors

| Plasmid: | Colonies/nM Methotrexate | | | |
|---|---|---|---|---|
| | 0 nM | 10 nM | 25 nM | 50 nM |
| PG8.5 | 206 | 65 | 8 | 3 |
| PG5.7ΔS | 224 | 57 | 6 | 3 |
| PG.2SE1.8 | 168 | 28 | 0 | 2 |
| PG.2SH1.2 | 51 | 2 | 0 | 1 |
| PG.2 | 85 | 22 | 1 | 0 |

These data indicate that the 1.8 kb Ecor1 to Swa1 fragment contained in PG.2FE1.8 is essential for EASE function. Moreover the 0.6 kb Hpa1 to EcoR1 fragment contained in this region is critical for EASE activity (compare results with PG.2SH1.2 and PG.2). Plasmids with longer lengths of CHO genomic DNA, i.e., PG8.5 and PG5.7ΔS, gave greater colony formation at increased selective pressure (25 nM and 50 nM MTX) when compared with plasmid PG.2SE1.8. This differential colony formation at higher selective pressure indicates that the presence of longer stretches of CHO genomic DNA in a plasmid confers higher frequency of high expression than shorter stretches of CHO genomic DNA.

Example 10

Transient Expression Assays

Transient expression assays were done to determine if the expression augmenting activity is acting like a classical enhancer or promoter, which can increase expression in transiently expressed non-chromosomal DNA. Plasmid PGP8.5 and plasmid PG2.2, the former of which had been shown to have EASE activity, while the latter did not (as demonstrated in Example 7), were transiently transfected into CHO cells using a Lipofectamine™ technique as described previously. After 48 hrs. supernatants were collected and tested for TNFrFc expression using ELISA as previously described. In contrast to the stable expression experiment in Example 7, these two plasmids gave the same level of expression of recombinant TNFrFc in the transient expression assay (see table 6).

TABLE 6

Transient expression of TNFrFc

| Plasmid | Average TNFrFc (ng/ml[1]) |
|---|---|
| PG2.2 | 95.75 ± 41.97 |
| PG8.5 | 105.5 ± 26.02 |

1: n = 4

These data indicate that EASE function requires chromosomal integration unlike previously known enhancers and/or promoters.

Example 11

Reduction in Time Required for Protein Production

Flt-3L was expressed in CHO cells using three different expression vectors, pCDE (see "expression of recombinant proteins"), PG5.7 and PG5.7I. The vector PG5.7I is a derivative of PG5.7 which contains the murine encephalomyocarditis virus IRES cloned between the adenovirus tripartite leader and the DHFR cDNA of PG5.7, DXB11 CHO cells were transfected with the three Flt-3L expression plasmids described above using the Lipofectamine™ method and selected for DHFR expression in -GHT media. DHFR+ colonies were then pooled and plated in 0 nM, 25 nM, 50 nM aqnd 100 nM MTX and allowed to grow to confluence, at which time specific productivities of pools transfected with each construct was determined. The expression from each construct was similar at each MTX level, however the time required for completing the analysis was only four to five weeks for the cell pools made with the PG5.7I vector compared with seven to eight weeks required for the pCDE and PG5.7 vectors.

This trend (obtaining similar expression levels in shorter periods of time when EASE is present) has been observed with many different proteins, at least three expressed in the pCDE vector and more than six expressed with the PG5.7I vector. In general, it takes two to five weeks less time to produce recombinant protein using expression vectors containing EASE and IRES sequences compared with similar expression vectors containing the IRES sequence alone. Moreover, the cell pools developed with EASE were stable over time, and could be treated as cell lines for most purposes. It was possible to delay cloning steps until much later in the development process, which provided a significant advantage for obtaining large amounts of recombinant proteins in a short time period.

Example 12

Use of EASE in Production-scale Expression

Recombinant HuCD40L was expressed in CHO cells for manufacturing using the PG5.7I vector. Here DNA encoding a trimeric form of huCD40L was cloned into the PG5.7I vector and DNA from the resulting CD40L expression plasmid was transfected into CHO cells using Lipofectamine™. Cells were first selected for the DHFR+ phenotype, then pooled and selected in 50 nM MTX. Cells which grew in 50 nM MTX were cloned using a soft agar cloning method (Gibson et al., *BioTechniques* 15:594, 1993). Eighteen colonies were picked and screened for specific productivity of huCD40L and two cell lines were selected for suspension adaptation and production runs in fed batch bioreactor runs. During two production runs of 10 and 8 days each using, one of the cell lines (the 50-B4 line), cells maintained an average specific productivity of approximately 24 and 25 $\mu g/10^6$ cells/day respectively. The final titers were 1.02 and 1.09 g/L by ELISA, for the 10 day run and 8 day runs respectively. This example demonstrates that use of this vector in manufacturing developement represents an improvement in the art since high levels of recombinant protein expression were achieved in a scalable format with a minimum of screening (18 cell lines screened) and selection steps (two steps).

What is claimed is:

1. An isolated expression augmenting sequence element (EASE), selected from the group consisting of DNAs comprising nucleotides 46 through 14507, nucleotides 5980 through 14507, nucleotides 8671 through 14507, nucleotides 8671 through 10515, nucleotides 9277 through 10515, nucleotides 8672 through 12273, nucleotides 10100 through 14293 of SEQ ID NO: 1, fragments of the foregoing DNAs that have expression augmenting activity, DNAs complementary to the foregoing DNAs, DNAs that are at least about 80% identical in nucleotide sequence to the foregoing DNAs and that have expression augmenting activity, and combinations of the foregoing DNAs that have expression augmenting activity.

2. An EASE according to claim 1, selected from the group consisting of DNAs consisting essentially of nucleotides 46 through 14507, nucleotides 5980 through 14507, nucleotides 8671 through 14507, nucleotides 8671 through 10515, nucleotides 9277 through 10515, nucleotides 8672 through 12273, and nucleotides 10100 through 14923 of SEQ. ID. NO.:1.

3. An EASE according to claim 2, which is ligated to a DNA selected from the group consisting of DNAs comprising nucleotides 14290 through 14507 of SEQ. ID. NO.: 1 and nucleotides 12592 through 14507 of SEQ. ID. NO.: 1.

4. An expression vector comprising the EASE of claim 1.

5. An expression vector comprising the EASE of claim 2.

6. An expression vector comprising the EASE of claim 3.

7. A stable pool of host cells transformed with an expression vector according to claim 5.

8. A stable pool of host cells transformed with an expression vector according to claim 6.

9. An EASE according to claim 1, wherein the DNA comprises nucleotide 8671 to nucleotide 9276 of SEQ. ID. NO.:1.

10. An expression vector comprising the EASE of claim 9.

11. The expression vector according to claim 10 which is a bicistronic plasmid wherein a first exon encodes a protein of interest and a second exon encodes an amplifyable dominant selectable marker.

* * * * *